US011188730B1

(12) United States Patent
Kwon et al.

(10) Patent No.: US 11,188,730 B1
(45) Date of Patent: Nov. 30, 2021

(54) APPARATUS AND METHOD FOR ESTIMATING BIO-INFORMATION

(71) Applicant: SAMSUNG ELECTRONICS CO., LTD., Suwon-si (KR)

(72) Inventors: Yong Joo Kwon, Yongin-si (KR); Yeol Ho Lee, Anyang-si (KR); Joon Hyung Lee, Seongman-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 17/157,365

(22) Filed: Jan. 25, 2021

(30) Foreign Application Priority Data

Sep. 2, 2020 (KR) .................. 10-2020-0111847

(51) Int. Cl.
G06K 9/00 (2006.01)
G06F 3/041 (2006.01)
G06F 3/042 (2006.01)

(52) U.S. Cl.
CPC ......... G06K 9/0004 (2013.01); G06F 3/0421 (2013.01); G06F 3/04166 (2019.05); G06K 9/00087 (2013.01); G06K 9/00912 (2013.01); G06K 2009/0006 (2013.01); G06K 2009/00939 (2013.01)

(58) Field of Classification Search
CPC ............. G06K 9/0004; G06K 9/00087; G06K 9/00912; G06K 2009/0006; G06K 2009/00939; G06F 3/04166; G06F 3/0421
See application file for complete search history.

(56) References Cited

U.S. PATENT DOCUMENTS

| 6,921,367 | B2 | 7/2005 | Mills |
| 8,095,211 | B2 | 1/2012 | Tamura et al. |
| 8,187,453 | B2 | 5/2012 | Wallace-Davis et al. |
| 8,798,702 | B2 | 8/2014 | Trumble |
| 10,271,745 | B2 | 4/2019 | Gu et al. |
| 10,383,576 | B2 | 8/2019 | Hall et al. |
| 10,485,461 | B2 | 11/2019 | Chang et al. |
| 10,595,757 | B2 | 3/2020 | Lee et al. |

(Continued)

FOREIGN PATENT DOCUMENTS

| EP | 3 275 364 A1 | 1/2018 |
| KR | 102005312 B1 | 7/2019 |

OTHER PUBLICATIONS

Communication dated Aug. 25, 2021, issued by the European Patent Office in European Application No. 21161790.7.

Primary Examiner — Abhishek Sarma
(74) Attorney, Agent, or Firm — Sughrue Mion, PLLC

(57) ABSTRACT

Example embodiments relate to an apparatus for non-invasively estimating bio-information is provided. An apparatus for estimating bio-information may include a sensor part including a pixel array of pixels, each pixel having a light source and a detector; and a processor configured to, based on an object being in contact with the sensor part, drive the sensor part based on a first sensor configuration; obtain contact information of the object based on an amount of light received by each pixel according to the first sensor configuration; determine a second sensor configuration based on the contact information; drive the sensor part based on the second sensor configuration; and estimate the bio-information based on light signals obtained according to the second sensor configuration.

25 Claims, 13 Drawing Sheets

(56) References Cited

U.S. PATENT DOCUMENTS

| | | | |
|---|---|---|---|
| 2009/0018463 A1* | 1/2009 | Tamura | A61B 5/0059 600/547 |
| 2012/0253153 A1* | 10/2012 | Trumble | A61B 5/14551 600/324 |
| 2017/0360316 A1* | 12/2017 | Gu | A61B 5/6824 |
| 2018/0028097 A1* | 2/2018 | Chang | A61B 5/1455 |
| 2018/0132766 A1* | 5/2018 | Lee | G01N 21/474 |
| 2019/0200866 A1 | 7/2019 | Eom et al. | |
| 2020/0037956 A1 | 2/2020 | Kang et al. | |
| 2020/0093377 A1 | 3/2020 | Kwon et al. | |
| 2020/0196935 A1 | 6/2020 | Eom et al. | |
| 2020/0253558 A1 | 8/2020 | Nam et al. | |

\* cited by examiner

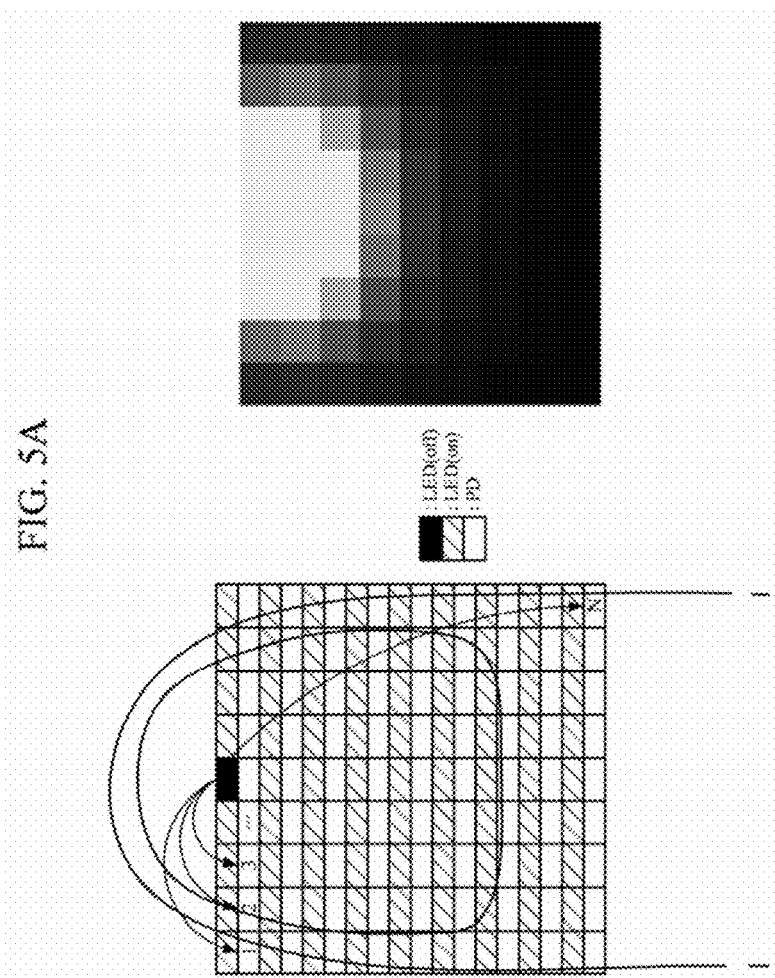

APPARATUS AND METHOD FOR ESTIMATING BIO-INFORMATION

CROSS-REFERENCE TO RELATED APPLICATION(S)

This application claims priority to Korean Patent Application No. 10-2020-0111847, filed on Sep. 2, 2020, in the Korean Intellectual Property Office, the entire disclosure of which is incorporated herein by reference for all purposes.

BACKGROUND

1. Field

Example embodiments of the present disclosure relate to an apparatus and method for non-invasively estimating bio-information.

2. Description of Related Art

According to a general method of non-invasively measuring triglycerides, triglyceride concentrations in blood are estimated by placing a measuring device, having a light source and an optical sensor, on blood vessels and by measuring signals of scattered light passing through blood. A change in blood triglyceride concentration leads to a change in scattering coefficient, such that the change in the scattering coefficient may be obtained from a change in the scattered light signals, and the blood triglyceride concentration may be estimated based on the change in the scattering coefficient.

SUMMARY

According to an aspect of an example embodiment, an apparatus for estimating bio-information may include a sensor part including a pixel array of pixels, each pixel having a light source and a detector; and a processor configured to, based on an object being in contact with the sensor part, drive the sensor part based on a first sensor configuration; obtain contact information of the object based on an amount of light received by each pixel according to the first sensor configuration; determine a second sensor configuration based on the contact information; drive the sensor part based on the second sensor configuration; and estimate the bio-information based on light signals obtained according to the second sensor configuration.

The first sensor configuration may include at least one of a time-division driving method, a sequential driving method, a simultaneous driving method, a driving order, a light source intensity, and a duration.

The processor may obtain the contact information based on at least one of a pixel having an amount of light being greater than or equal to a predetermined threshold value, a pixel having an amount of light being greater than or equal to a predetermined percentage of an average value of a total amount of light, a pixel having an amount of light being greater than or equal to a predetermined percentage of a maximum amount of light, and a pixel having an amount of light being greater than or equal to a predetermined percentage of an average value of an amount of light falling within a predetermined range of the maximum amount of light.

The processor may obtain the contact information including at least one of a contact area of the object, a center point of the contact area, a fingerprint center point, and a contact direction.

The processor may, based on the contact information, determine a light source pixel and a detector pixel of the second sensor configuration.

The processor may determine one or more pixels, located at predetermined positions in the contact direction, to be light source pixels of the second sensor configuration, among pixels in the contact area; and determine one or more pixels, located within a predetermined range from the center point of the contact area or the fingerprint center point, to be detector pixels of the second sensor configuration.

The processor may map a reference area, a reference direction, and a reference center point of a pre-defined reference sensor configuration to the contact area, the contact direction, and the center point of the contact area; and based on the mapping, determine pixels corresponding to light source pixels of the pre-defined reference sensor configuration to be the light source pixels of the second sensor configuration, and pixels corresponding to detector pixels of the pre-defined reference sensor configuration to be detector pixels of the second sensor configuration.

The sensor part may obtain a fingerprint image based on the object being in contact with the sensor part, and the processor may obtain the contact information based on the fingerprint image.

The processor may, in response to the fingerprint center point not being located within a predetermined range of the sensor part, control an output interface to guide a user to place the object on the sensor part.

The processor may calculate a scattering coefficient based on the light signals obtained according to the second sensor configuration; and estimate the bio-information based on the scattering coefficient.

The processor may, in response to the light signals being obtained according to the second sensor configuration, calculate a similarity between the light signals; and select light signals, having the similarity being greater than or equal to a first threshold value, as light signals for estimating the bio-information.

The processor may, in response to the light signals being obtained according to the second sensor configuration, calculate a similarity between the light signals; and exclude light signals, having the similarity being less than or equal to a second threshold value, as light signals for estimating the bio-information.

The bio-information may include at least one of triglyceride, body fat percentage, body water, blood glucose, cholesterol, carotenoid, protein, and uric acid.

According to an aspect of an example embodiment, a method of estimating bio-information may include, based on an object being in contact with a sensor part, driving the sensor part based on a first sensor configuration; obtaining contact information of the object based on an amount of light received by each pixel of the sensor part according to the first sensor configuration; determining a second sensor configuration based on the contact information; driving the sensor part based on the second sensor configuration; and estimating the bio-information based on light signals obtained according to the second sensor configuration.

The obtaining the contact information may include obtaining the contact information based on at least one of a pixel having an amount of light being greater than or equal to a predetermined threshold value, a pixel having an amount of light being greater than or equal to a predetermined percentage of an average value of a total amount of light, a pixel having an amount of light being greater than or equal to a predetermined percentage of a maximum amount of light, and a pixel having an amount of light being greater than or equal to a predetermined percentage of an average value of an amount of light falling within a predetermined range of the maximum amount of light.

The obtaining the contact information may include obtaining the contact information including at least one of a contact area of the object, a center point of the contact area, a fingerprint center point, and a contact direction.

The determining the second sensor configuration may include determining one or more pixels, located at predetermined positions in the contact direction, to be light source pixels of the second sensor configuration, among pixels in the contact area; and determining one or more pixels, located within a predetermined range from the center point of the contact area or the fingerprint center point, to be detector pixels of the second sensor configuration.

The determining the second sensor configuration may include mapping a reference area, a reference direction, and a reference center point of a pre-defined reference sensor configuration to the contact area, the contact direction, and the center point of the contact area; and based on the mapping, determining pixels corresponding to light source pixels of the pre-defined reference sensor configuration to be the light source pixels of the second sensor configuration, and pixels corresponding to detector pixels of the pre-defined reference sensor configuration to be the detector pixels of the second sensor configuration.

The method may include obtaining a fingerprint image based on the object being in contact with the sensor part.

The obtaining the contact information may include obtaining the contact information based on the fingerprint image.

The method may include, in response to the fingerprint center point not being located within a predetermined range of the sensor part, controlling an output interface to guide a user to place the object on the sensor part.

The estimating the bio-information may include calculating a scattering coefficient based on two or more light signals obtained by the sensor part; and estimating the bio-information based on the scattering coefficient.

The estimating the bio-information may include, in response to the light signals being obtained by the sensor part, calculating a similarity between the light signals; and selecting light signals, having the similarity being greater than or equal to a first threshold value, as light signals for estimating the bio-information.

The estimating of the bio-information may include, in response to the light signals being obtained by the sensor part, calculating a similarity between the light signals; and excluding light signals, having the similarity being less than or equal to a second threshold value, as light signals for estimating the bio-information.

BRIEF DESCRIPTION OF THE DRAWINGS

The above and other aspects, features, and advantages of certain example embodiments of the present disclosure will be more apparent from the following description taken in conjunction with the accompanying drawings, in which:

FIGS. 5A and 5B are diagrams explaining an example of estimating bio-information;

DETAILED DESCRIPTION

Figure 1:
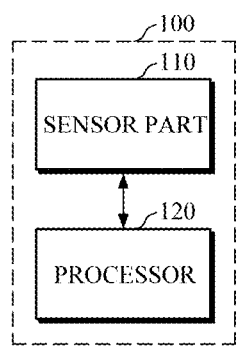
FIG. 1 is a block diagram illustrating an apparatus for estimating bio-information according to an example embodiment.

Details of example embodiments are provided in the following detailed description and drawings. Advantages and features of the present disclosure, and methods of achieving the same will be more clearly understood from the following example embodiments described in detail with reference to the accompanying drawings. Throughout the drawings and the detailed description, unless otherwise described, the same drawing reference numerals will be understood to refer to the same elements, features, and structures.

It will be understood that although the terms "first," "second," etc. may be used herein to describe various elements, these elements should not be limited by these terms. These terms are only used to distinguish one element from another. Also, the singular forms of terms are intended to include the plural forms of the terms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and they may be implemented by using hardware, software, or a combination thereof. As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Hereinafter, example embodiments of an apparatus and method for estimating bio-information will be described in detail with reference to the accompanying drawings. Various example embodiments of the apparatus for estimating bio-information may be mounted in terminals, such as a smartphone, a tablet personal computer (PC), a desktop computer, a laptop computer, etc., wearable devices, and the like. In this case, examples of the wearable devices may include a wristwatch-type wearable device, a bracelet-type wearable device, a wristband-type wearable device, a ring-type wearable device, a glasses-type wearable device, a headband-type wearable device, etc., but the wearable devices are not limited thereto.

FIG. 1 is a block diagram illustrating an apparatus for estimating bio-information according to an example embodiment.

Referring to FIG. 1, the apparatus 100 for estimating bio-information includes a sensor part 110 and a processor 120.

The sensor part 110 includes a pixel array having a plurality of pixels. Each pixel may include one or more light sources for emitting light onto an object, and one or more detectors for detecting light scattered or reflected from the object. Further, a partition wall for blocking light may be disposed between the pixels and/or between the light source and the detector of each pixel.

The light source may include a light emitting diode (LED), a laser diode (LD), a phosphor, and the like. If each pixel includes a plurality of light sources, the light sources may emit light of different wavelengths. The detector may detect light returning after the light, emitted by the light source, is absorbed into or reflected or scattered from the object OBJ. The detector may include a photodiode, a photo transistor (PTr), an image sensor, and the like.

In addition, the sensor part 110 may further include a fingerprint sensor. The fingerprint sensor may be disposed at the top or bottom of the pixel array of the sensor part 110. The fingerprint sensor may acquire an image of wrinkles on a body part being in contact with the pixel array. However, the wrinkle image is not limited thereto, and may be acquired by manufacturing each pixel of the pixel array in a sufficiently small size and by scan driving all of the pixels in the pixel array. Here, the body part may be any part of the body in which a photoplethysmography (PPG) signal may be detected therefrom, and the following description will be given using a finger as an example of the body part, such that wrinkles on the body part may be specified as a fingerprint, and a "fingerprint center point," described in relation to the fingerprint, may be an example of a characteristic point of wrinkles on a body part.

The processor 120 may be electrically connected to the sensor part 110, and may control the sensor part 110 in response to a request for estimating bio-information. Further, the processor 120 may receive a light signal from the sensor part 110, and may estimate bio-information based on the received light signal. In this case, the bio-information may include triglyceride, body fat percentage, body water, blood glucose, cholesterol, carotenoid, protein, uric acid, and the like, but is not limited thereto. The following description will be given using triglyceride as an example.

For example, in response to a request for estimating bio-information, the processor 120 may drive the sensor part 110 based on a first sensor configuration. In this case, the first sensor configuration may include information, such as a driving method, a driving order, a light source intensity, a duration, etc., of the sensor part 110. In addition, the processor 120 may obtain contact information of the object based on the light signal obtained by the sensor part 110 based on the first sensor configuration. In this case, the contact information may include a contact area of the object, a center point of the contact area, a fingerprint center point, a contact direction, etc., but is not limited thereto.

Based on obtaining the contact information as described above, the processor 120 may determine a second sensor configuration, and may drive the sensor part 110 based on the determined second sensor configuration. The second sensor configuration may be determined to include various combinations of light source pixels having light sources to be driven and detector pixels having detectors to be driven among all of the pixels of the sensor part 110, with the light sources and the detectors being disposed at different distances from each other so that scattered light signals may be obtained via two or more different paths. For example, the combinations of pixels may include a combination of one light source pixel and a plurality of detector pixels, a combination of a plurality of light source pixels and one detector pixel, a combination of a plurality of light source pixels and a plurality of detector pixels, and the like. In this case, the light source pixels may refer to pixels having light sources to be driven, and the detector pixels may refer to pixels having detectors to be driven, in the array of the pixels.

In addition, based on the sensor part 110 obtaining the light signal based on the second sensor configuration, the processor 120 may estimate bio-information based on the obtained light signal. The processor 120 may amplify the light signal obtained by the sensor part 110 by using an amplifier, or may convert the signal into a digital signal by using an analog-digital converter, and the like.

Figure 2:
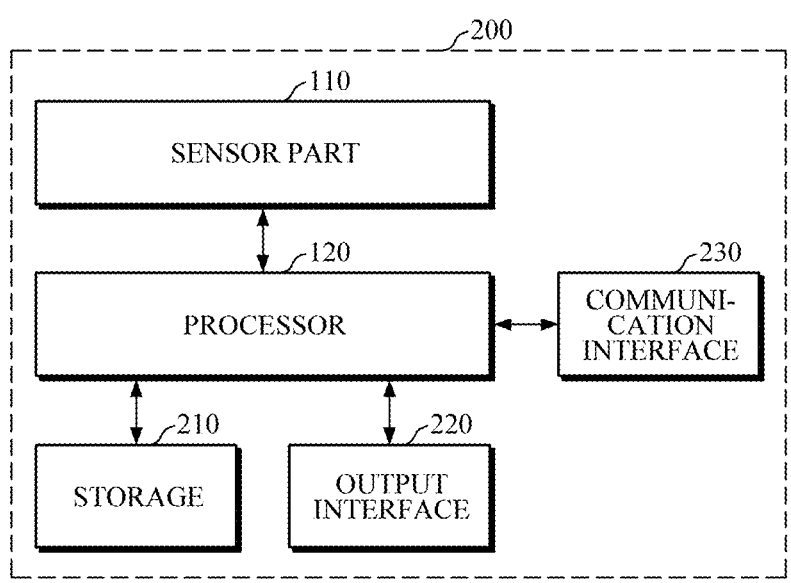
FIG. 2 is a block diagram illustrating an apparatus for estimating bio-information according to another example embodiment.

FIG. 2 is a block diagram illustrating an apparatus for estimating bio-information according to another example embodiment.

Referring to FIG. 2, the apparatus 200 for estimating bio-information according to another example embodiment includes the sensor part 110, the processor 120, a storage 210, an output interface 220, and a communication interface 230. The sensor part 110 and the processor 120 are described above.

The storage 210 may store information related to estimating bio-information. For example, the storage 210 may store a light signal and/or an estimated bio-information value. Further, the storage 210 may store a first sensor configuration, a reference sensor configuration, a second sensor configuration, criteria for determining the second sensor configuration, criteria for obtaining contact information, user characteristic information, and the like. In this case, the user characteristic information may include a user's age, gender, health condition, and the like.

The storage 210 may include at least one storage medium of a flash memory type memory, a hard disk type memory, a multimedia card micro type memory, a card type memory (e.g., a secure digital (SD) memory, an eXtreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The output interface 220 may provide processing results of the processor 120 for a user. For example, the output interface 220 may display an estimated bio-information value on a display. In this case, if the estimated bio-information value falls outside of a normal range, the output interface 220 may provide a user with warning information by changing color, line thickness, etc., or displaying the abnormal value along with a normal range, so that the user may easily recognize the abnormal value. Further, along with or without the visual display, the output interface 220 may provide a bio-information estimation result in a non-visual manner such as by voice, vibrations, tactile sensation, and the like, using a voice output module such as a speaker, or a haptic module, and the like.

The communication interface 230 may communicate with an external device to transmit and receive various data related to estimating bio-information. In this case, the external device may include an information processing device such as a smartphone, a tablet PC, a desktop computer, a laptop computer, and the like. For example, the communication interface 230 may transmit a bio-information estimation result to a user's smartphone, and the like, so that the user may manage and monitor the bio-information estimation result by using a device having a relatively high performance.

In this case, the communication interface 230 may communicate with the external device by using various wired or wireless communication techniques, such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, 3G communication, 4G communication, 5G communication, and the like. However, is the foregoing communication techniques are examples, and are not intended to be limiting.

Figure 3:
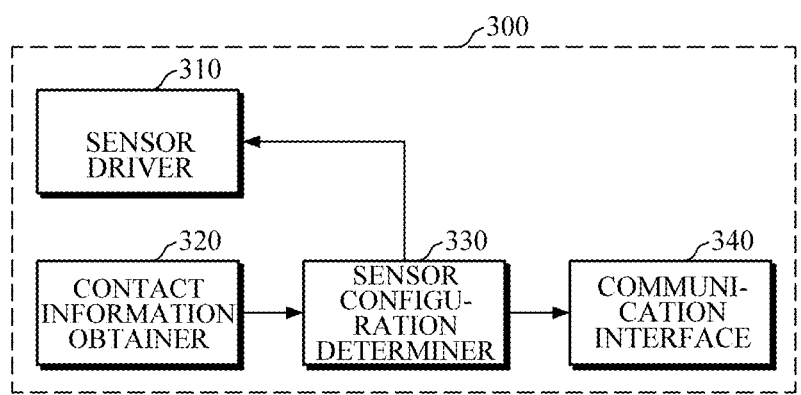
FIG. 3 is a block diagram illustrating a configuration of a processor according to an example embodiment.
Figure 4A:
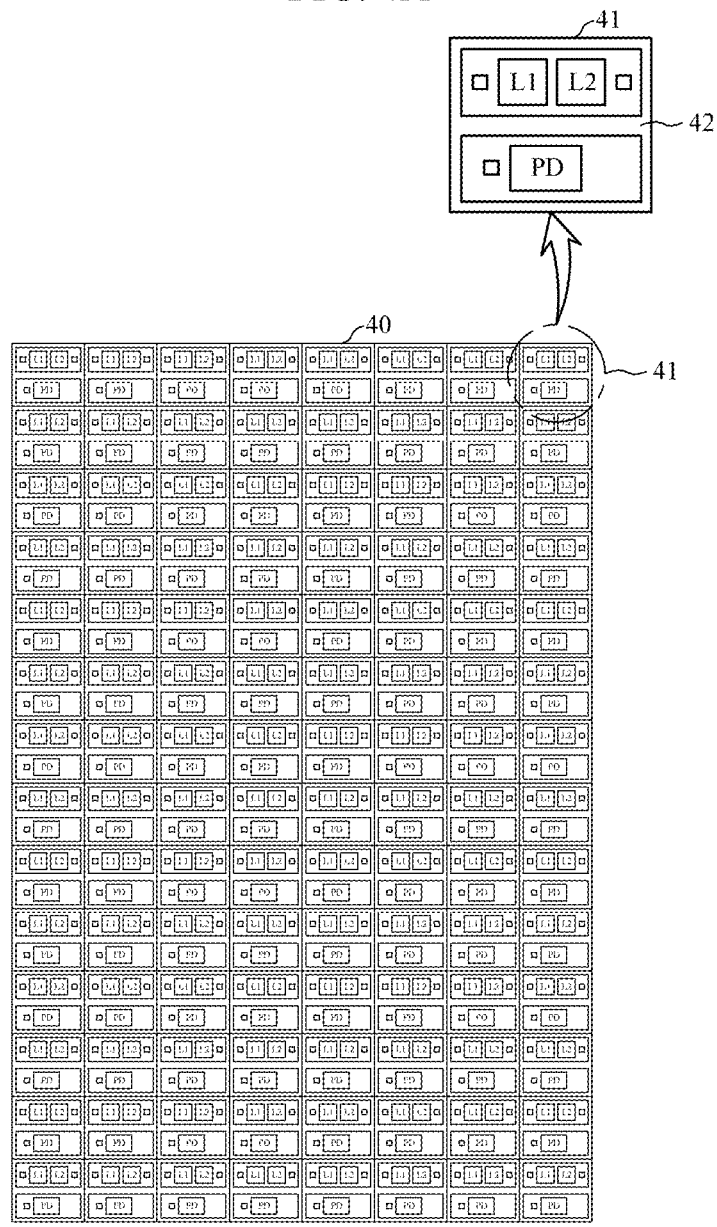
FIGS. 4A and 4B are diagrams explaining an example of obtaining contact information of an object.
Figure 4B:
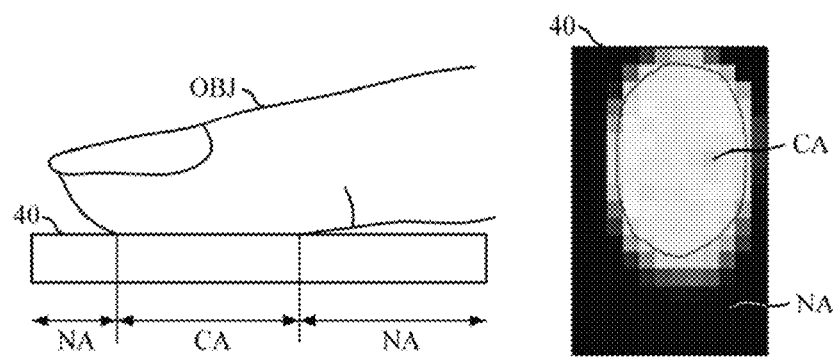
Figure 4C:
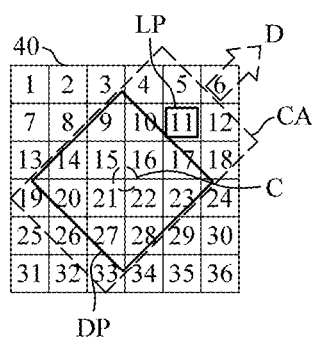
FIGS. 4C, 4D, and 4E are diagrams explaining an example of obtaining a second sensor configuration.
Figure 4D:
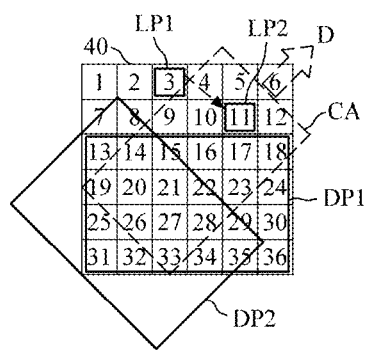
Figure 4E:
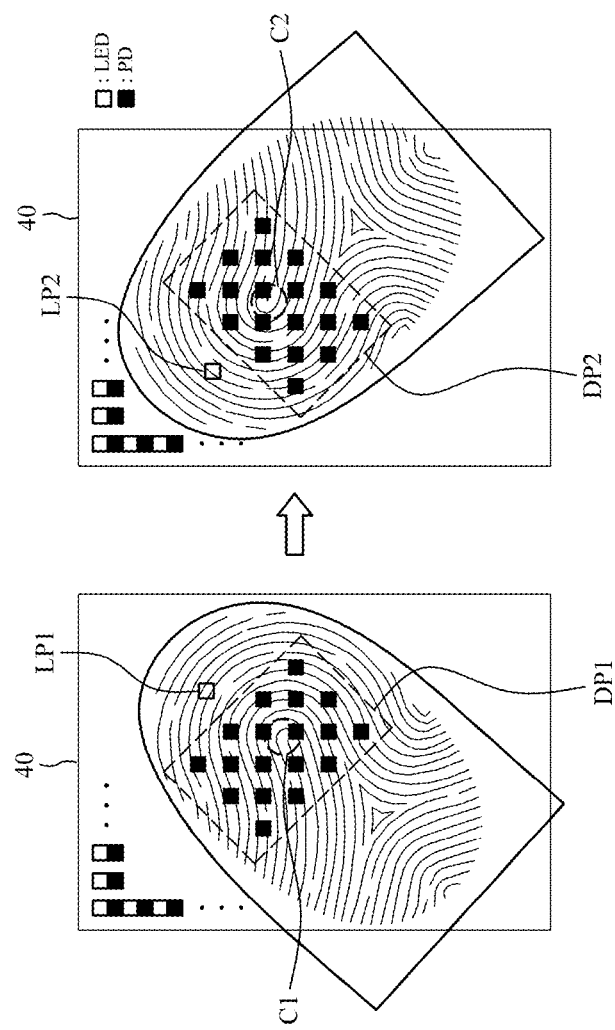
Figure 5B:
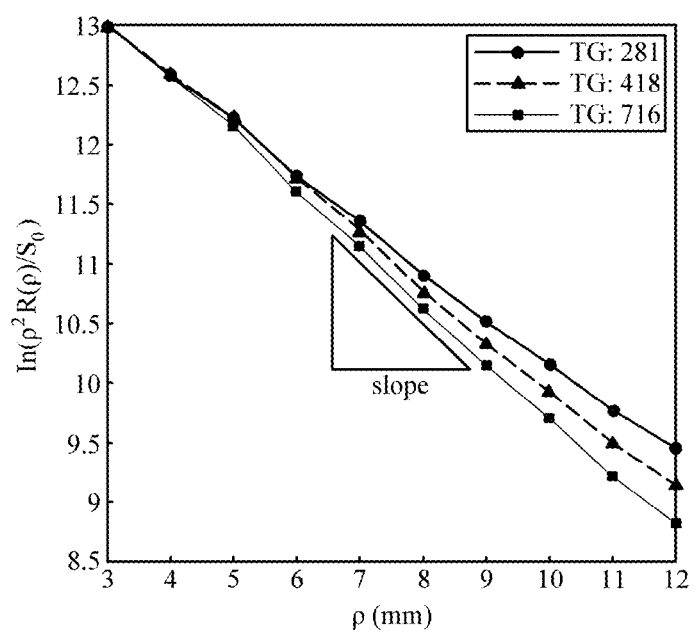

FIG. 3 is a block diagram illustrating a configuration of a processor according to an example embodiment. FIGS. 4A and 4B are diagrams explaining an example of obtaining contact information of an object. FIGS. 4C, 4D, and 4E are diagrams explaining an example of obtaining a second sensor configuration. FIGS. 5A and 5B are diagrams explaining an example of estimating bio-information.

Referring to FIG. 3, a processor 300 according to an embodiment includes a sensor driver 310, a contact information obtainer 320, a sensor configuration determiner 330, and an estimator 340.

Referring to FIG. 4A, the sensor part 110 may include a pixel array 40 having a plurality of pixels 41. Each pixel 41 may include one or more light sources L1 and L2 and a detector PD. In this case, a partition wall 42 may be disposed between the pixels 41 and/or between the light sources L1 and L2 and the detector PD of each pixel 41.

The sensor driver 310 may drive the pixel array 40 by referring to the first sensor configuration for obtaining contact information of a finger when the finger is placed on the sensor part 110. The first sensor configuration may include pixels 41 to be driven such as information on pixels to be driven for obtaining contact information in the entire pixel array 40. In this case, the pixels 41 to be driven may be set to all of the pixels 41 in the pixel array 40. However, the pixels 41 to be driven are not limited thereto; and by considering power consumption, required accuracy of estimation, and the like, the pixels 41 to be driven may be set to pixels 41 in some of the rows/columns such as, for example, pixels 41 in odd number/even number rows/columns. Further, the first sensor configuration may include a driving method, a driving order, a light source intensity, a duration, and the like. The driving method may be set to any one of, for example, sequential driving, time-division driving, and simultaneous driving.

By driving all the pixels 41 to be driven under the control of the sensor driver 310 by turning on the light sources of a specific driven pixel 41 and detecting light using the detector of the specific driven pixel 41, the sensor part 110 may scan a finger and may obtain light signals for all the driven pixels 41.

Referring to FIG. 4B, when the finger OBJ comes into contact with the pixel array 40 of the sensor part 110, the pixel array 40 of the sensor part 110 may be divided into a contact area (CA) that is in contact with the finger OBJ, and a non-contact area (NA) that is not in contact with the finger OBJ.

Based on the sensor part 110 obtaining the light signals by scanning the finger, the contact information obtainer 320 may obtain contact information of the finger based on the obtained light signals, as illustrated in FIG. 4B. For example, the contact information obtainer 320 may obtain, as the contact area CA, an area of pixels in which an amount of light received by the respective pixels is greater than or equal to a predetermined threshold value. Alternatively, the contact information obtainer 320 may obtain, as the contact area CA, an area of pixels in which an amount of light is greater than or equal to a predetermined percentage of an average value of total amounts of light received by the respective pixels, an area of pixels in which an amount of light is greater than or equal to a predetermined percentage of a maximum amount of light, or an area of pixels in which an amount of light is greater than or equal to a predetermined percentage of an average value of amounts of light falling within a predetermined range of the maximum amount of light. However, these are merely examples. Further, the contact information obtainer 320 may obtain a center point of the obtained contact area CA and/or a contact direction.

In addition, if the sensor part 110 obtains a fingerprint image, the contact information obtainer 320 may analyze the fingerprint image to obtain a fingerprint center point, a contact area and/or a contact direction.

The sensor configuration determiner 330 may determine a second sensor configuration for estimating bio-information based on the contact information. In this case, the second sensor configuration may include light source pixels having light sources to be driven for emitting light onto the object, and detector pixels having detectors to be driven for detecting light signals from the object. In this case, the light source pixels may be different from the detector pixels. The light source pixel may include at least one pixel 41, and the detector pixel may include a plurality of pixels 41 for detecting light scattered from different positions of the object.

Referring to FIG. 4C, the sensor configuration determiner 330 may determine a pixel 11, located at a predetermined position in a contact direction D, to be a light source pixel LP among the pixels of the pixel array 40 in a contact area CA. In this case, criteria for determining the light source pixel such as, for example, determining a pixel located at the foremost of the contact area CA, may be preset.

Further, the sensor configuration determiner 330 may determine, as a detector pixel DP, pixels 9, 10, 14, 15, 16, 17, 19, 20, 21, 22, 23, 27, and 28 located within a predetermined range from the center point C of the contact area. In this case, criteria for determining the detector pixel DP such as, for example, a predetermined range, a shape (e.g., circle, oval, polygon, etc.) of the predetermined range, and the like, may be preset. However, the criteria are not limited thereto, and the detector pixel PD may be defined as various pixels, such as all the pixels, all the pixels except the light source pixels LP, or all the pixels located below the light source pixels LP, and the like.

Referring to FIG. 4D, the sensor configuration determiner 330 may determine a light source pixel and a detector pixel of the second sensor configuration based on a pre-defined reference sensor configuration. For example, the reference sensor configuration may include a light source pixel LP1, a detector pixel DP1, and/or information on a reference center point in a reference area of the pixel array 40. In this case, the reference area may be, for example, the entire area of the pixel array 40, and the reference center point may be a center point of the pixel array 40, but is not limited thereto.

Based on the contact information obtainer 320 obtaining the contact area, the contact direction, and the center point of the contact area, the sensor configuration determiner 330 may map the reference center point to the center point of the contact area, and may turn the reference direction to the right in the contact direction D, to map the reference area to the contact area CA so that the reference area may overlap the contact area CA. Based on the mapping, the sensor configuration determiner 330 may determine the pixel 11, corresponding to the light source pixel LP1, and pixels 7, 8, 13, 14, 15, 19, 20, 21, 22, 25, 26, 27, 28, 29, 31, 32, 33, 34, and 35, corresponding to the detector pixel DP1, of the reference sensor configuration to be a light source pixel LP2 and a detector pixel DP2, respectively, of the second sensor configuration. However, this is merely an example.

FIG. 4E illustrates examples of determining the second sensor configuration based on the fingerprint image. As illustrated in FIG. 4E, the sensor configuration determiner 330 may adaptively determine the light source pixels LP1 and LP2 and the detector pixels DP1 and DP2 based on the fingerprint area, fingerprint direction, and fingerprint center points C1 and C2. In this case, if a fingerprint center point is not located within a predetermined range of the sensor part 110, the sensor configuration determiner 330 may guide a user to place the finger on the sensor part 110 again. In this case, the predetermined range may be preset.

As described above, according to the example embodiments of the present disclosure, even when the contact area and/or the contact direction of the finger are changed, the light source pixels and the detector pixels of the second sensor configuration may be determined adaptively, such that light signals may be detected at a predetermined position of the finger or at an actual contact position of the finger, thereby improving accuracy in estimating bio-information.

Based on the sensor configuration determiner 330 determining the second sensor configuration, the sensor driver 310 may drive the light source pixels and the detector pixels of the sensor part 110 based on the second sensor configuration.

Based on the sensor part 110 obtaining a plurality of light signals of a plurality of light paths based on the second sensor configuration, the estimator 340 may estimate bio-information based on the obtained plurality of light signals. FIG. 5A illustrates an example of a map of light intensity for each distance when a plurality of detector pixels are located at different distances from the light source pixels.

The estimator 340 may estimate bio-information based on the plurality of light signals obtained at different distances. For example, the estimator 340 may calculate a scattering coefficient by using the light signals obtained at each distance, and may estimate bio-information by using the calculated scattering coefficient. In this case, the scattering coefficient indicates a decrease in light intensity due to scattering of light when light emitted by the light source travels a unit length, and may be defined as, for example, a ratio of intensities of scattered light signals detected by a plurality of detectors or a value proportional to the ratio. Further, the scattering coefficient may be calculated by considering distances of the respective detectors from the light sources. Alternatively, the estimator 340 may calculate a scattering coefficient by obtaining a representative value of the plurality of light signal intensities. In this case, the representative value of the plurality of light signal intensities may be calculated based on various criteria, such as a maximum signal intensity value, a mean value or a median value of the signal intensities, and the like.

For example, when calculating the scattering coefficient by using one scattered light signal detected by one detector, the estimator 340 may calculate the scattering coefficient by using, for example, the following Equations 1 and 2.

$$\ln\left\{\rho^2 \frac{R(\rho)}{S_0}\right\} = -\mu_{eff}\rho + \ln\frac{3\mu_a}{2\pi\mu_{eff}} \qquad [\text{Equation 1}]$$

$$\ln\left\{\rho^3 \frac{R(\rho)}{S_0}\right\} = -\mu_{eff}\rho + \ln\frac{1}{2\pi\mu_x^2} \qquad [\text{Equation 2}]$$

Herein, $R(\rho)$ denotes the intensity of light detected by a detector located at a distance of $\rho$ from the light source; p denotes the distance between the light source and the detector; $\mu_a$ denotes an absorption coefficient; $\rho_{eff}$ denotes an effective attenuation coefficient; $S_0$ denotes the intensity of light emitted by the light source; and $\mu_s$ denotes the scattering coefficient.

In yet another example, when calculating the scattering coefficient by using two signals of scattered light detected by two detectors disposed at different distances after the light emitted by the light source, the estimator 340 may calculate the scattering coefficient by using the following Equation 3.

$$\mu_x^* = \frac{1}{3\mu_a}\left\{\frac{1}{\rho_2 - \rho_1}\ln\frac{\rho_1^2 R(\rho_1)}{\rho_2^2 R(\rho_2)}\right\}^2 \qquad [\text{Equation 3}]$$

Herein, $\rho_1$ denotes a distance between the light source and a first detector; $\rho_2$ denotes a distance between the light source and a second detector; $R(\rho_1)$ denotes the intensity of light detected by the first detector; $R(\rho_2)$ denotes the intensity of light detected by the second detector; and $\mu_s$ denotes the scattering coefficient. The equation for calculating the scattering coefficient may be defined differently according to the number of detectors detecting light emitted by the light source.

Based on the plurality of detectors obtaining the plurality of scattered light signals, the estimator 340 may select some of the obtained light signals, and may calculate the scattering coefficient by using the selected light signals. For example, the estimator 340 may calculate a similarity between the plurality of scattered light signals, and may select light signals having a calculated similarity greater than or equal to a first threshold value. Alternatively, the estimator 340 may calculate a similarity between the plurality of scattered light signals, and may calculate the scattering coefficient by using light signals which remain after excluding light signals having a calculated similarity less than or equal to a second threshold value. In this case, the similarity may include at least one of Euclidean distance, Pearson correlation coefficient, Spearman correlation coefficient, and Cosine similarity.

Based on calculating the scattering coefficient, the estimator 340 may obtain a triglyceride value by using an estimation model which defines a correlation between the scattering coefficient and bio-information such as triglycerides. In this case, the estimation model may be expressed in the form of linear/non-linear functions or a matching table indicating a correlation between the scattering coefficient and a bio-information estimation value. FIG. 5B illustrates a correlation between a value of the left side of the above Equation 1 and a distance according to a change in triglyceride levels. As illustrated in FIG. 5B, as a blood triglyceride concentration changes, a scattering coefficient of blood also changes, such that a scattered light signal may change with distance between the light source and the detector. As described above, an estimation model may be pre-defined by using the correlation between the scattering coefficient and the triglyceride concentration.

Figure 6:
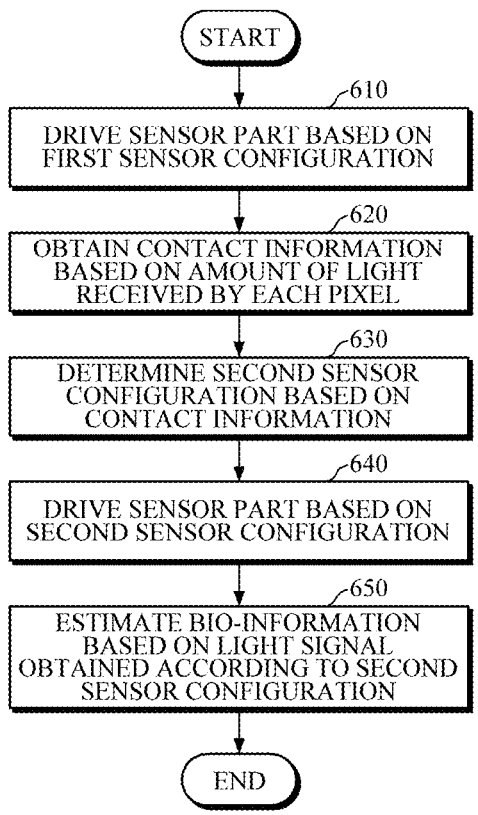
FIG. 6 is a flowchart illustrating a method of estimating bio-information according to an example embodiment.

FIG. 6 is a flowchart illustrating a method of estimating bio-information according to an example embodiment. The method of FIG. 6 is an example of a method of estimating bio-information which is performed by the apparatuses 100 and 200 for estimating bio-information according to the example embodiments of FIG. 1 or 2.

Referring to FIG. 6, in response to a request for estimating bio-information, the apparatus for estimating bio-information may drive a sensor part based on a first sensor configuration to detect a scattered light signal from an object in operation 610. In this case, the apparatus for estimating bio-information may control driving of the sensor part based on a pre-defined first sensor configuration. In this case, if the sensor part includes a fingerprint sensor, the apparatus for estimating bio-information may obtain a fingerprint image.

Then, the apparatus for estimating bio-information may obtain contact information in operation 620 based on the amount of light received by each pixel, which is obtained by scanning the object, being in contact with the sensor part, based on the first sensor configuration, and/or the fingerprint image. In this case, the contact information may include a contact area, a center point of the contact area, a fingerprint center point, a contact direction, and the like.

Subsequently, the apparatus for estimating bio-information may determine a second sensor configuration based on the obtained contact information in operation 630. In this case, the second sensor configuration may include information on light source pixels and detector pixels, disposed at different distances from the light source pixels, so that scattered light signals may be obtained at various positions spaced apart by different distances from the light sources.

For example, the apparatus for estimating bio-information may determine one or more pixels, located at predetermined positions in a contact direction, to be light source pixels of the second sensor configuration, among pixels in a contact area; and may determine all pixels or pixels, located within a predetermined range from the center point of the contact area or the fingerprint center point, to be detector pixels of the second sensor configuration.

In another example, the apparatus for estimating bio-information may map a reference area, a reference direction, and a reference center point of the pre-defined reference sensor configuration to the contact area, the contact direction, and the center point of the contact area. Based on the mapping, the apparatus for estimating bio-information may determine pixels, corresponding to light source pixels, and pixels corresponding to detector pixels, of the reference sensor configuration to be the light source pixels and the detector pixels, respectively, of the second sensor configuration.

Next, the apparatus for estimating bio-information may detect a plurality of scattered light signals by driving the sensor part based on the second sensor configuration in operation 640.

Then, the apparatus for estimating bio-information may estimate bio-information based on the light signals obtained according to the second sensor configuration in operation 650. For example, the apparatus for estimating bio-information may calculate a scattering coefficient based on the light signals, and may estimate bio-information by using a pre-defined estimation model. In this case, if a plurality of light signals are obtained, the apparatus for estimating bio-information may calculate a similarity between the light signals, and may calculate the scattering coefficient by using only the light signals having the calculated similarity greater than or equal to a first threshold value. Alternatively, the apparatus for estimating bio-information may calculate the scattering coefficient by using light signals which remain after excluding light signals having the calculated similarity less than or equal to a second threshold value.

Figure 7:
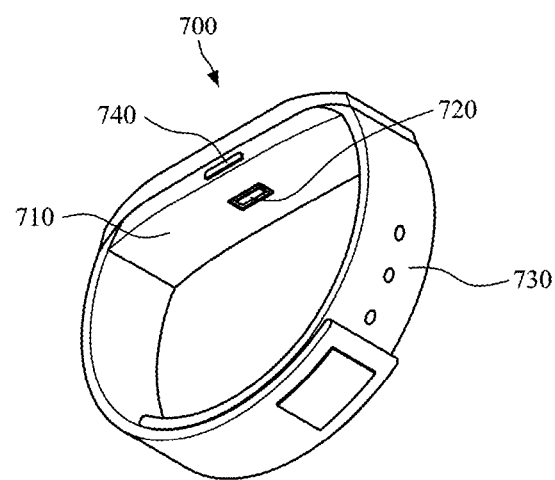
FIG. 7 is a diagram illustrating an example of a wearable device.

FIG. 7 is a diagram illustrating an example of a wearable device. The aforementioned example embodiments of the apparatuses 100 and 200 for estimating bio-information may be mounted in the wearable device.

Referring to FIG. 7, the wearable device 700 includes a main body 710 and a strap 730.

The strap 730, which is connected to both ends of the main body 710, may be flexible so as to be wrapped around a user's wrist. The strap 730 may be composed of a first strap and a second strap which are separated from each other. Respective ends of the first strap and the second strap are connected to the main body 710, and the other ends thereof may be connected to each other via a connecting means. In this case, the connecting means may be formed as magnetic connection, Velcro connection, pin connection, and the like, but is not limited thereto. Further, the strap 730 is not limited thereto, and may be integrally formed as a non-detachable band.

In this case, air may be injected into the strap 730, or the strap 730 may be provided with an air bladder to have elasticity according to a change in pressure applied to the wrist, and may transmit the change in pressure of the wrist to the main body 710.

A battery may be embedded in the main body 710 or the strap 730 to supply power to the wearable device 700.

The main body 710 may include a sensor part 720 mounted on one side thereof. The sensor part 720 may include a pixel array having pixels, each of which includes a light source and a detector. In addition, the sensor part 720 may further include a fingerprint sensor for obtaining a fingerprint image when the finger comes into contact with the sensor pail 720.

A processor may be mounted in the main body 710. The processor may be electrically connected to modules mounted in the wearable device 700. The processor may estimate bio-information based on light signals obtained by the sensor part 720. In this case, by controlling the sensor part 720 based on a first sensor configuration, the processor may scan the object and may obtain contact information of the object. Further, the processor may determine a second sensor configuration based on the contact information, and may control the sensor part 720 based on the determined second sensor configuration. As described above, based on obtaining the light signals based on the second sensor configuration, the processor may obtain bio-information by calculating a scattering coefficient based on the obtained light signals.

Further, the main body 710 may include a storage which stores reference information for estimating bio-information and information processed by various modules thereof.

In addition, the main body 710 may include a manipulator 740 which is provided on one side surface of the main body 710, and receives a user's control command and transmits the received control command to the processor. The manipulator 740 may have a power button to input a command to turn on/off the wearable device 700.

Further, a display for outputting information to a user may be mounted on a front surface of the main body 710. The display may have a touch screen for receiving touch input. The display may receive a user's touch input and transmit the touch input to the processor, and may display processing results of the processor.

Moreover, the main body 710 may include a communication interface for communication with an external device.

The communication interface may transmit a bio-information estimation result to the external device such as a user's smartphone.

Figure 8:
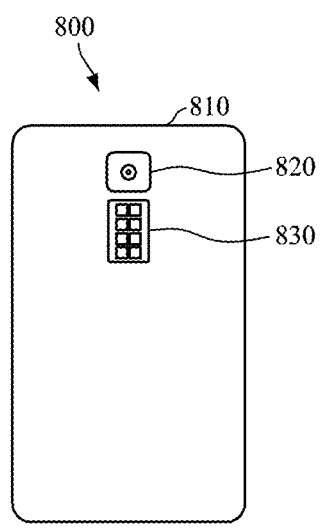
FIG. 8 is a diagram illustrating an example of a smart device.

FIG. 8 is a diagram illustrating an example of a smart device. In this case, the smart device may include a smartphone, a tablet PC, and the like. The smart device may include functions of the aforementioned example embodiments of the apparatuses 100 and 200 for estimating bio-information.

Referring to FIG. 8, the smart device 800 includes a main body 810 and a sensor part 830 mounted on one surface of the main body 810. For example, the sensor part 830 may further include a fingerprint sensor.

Moreover, a display may be mounted on a front surface of the main body 810. The display may visually output a bio-information estimation result, a health condition evaluation result, and the like. The display may include a touch screen, and may receive information input through the touch screen and transmit the information to a processor.

The main body 810 may include an image sensor 820 as illustrated in FIG. 8. The image sensor 820 may capture various images, and may acquire, for example, a fingerprint image of a finger being in contact with the sensor part 830.

The processor may be mounted in the main body 810 to be electrically connected to various modules thereof, and may control operations of the modules. The processor may control the sensor part based on a first sensor configuration for obtaining contact information, and may obtain contact information based on light signals obtained according to the first sensor configuration. In addition, the processor may adaptively determine a second sensor configuration based on the contact information, and may control the sensor part according to the determined second sensor configuration. In this manner, the processor may obtain light signals at contact positions of the object, thereby improving accuracy in estimating bio-information.

The example embodiments may be implemented by computer-readable code written on a non-transitory computer-readable medium and executed by a processor. The non-transitory computer-readable medium may be any type of recording device in which data is stored in a computer-readable manner.

Examples of the computer-readable medium include a ROM, a RAM, a CD-ROM a magnetic tape, a floppy disc, an optical data storage, and a carrier wave (e.g., data transmission through the Internet). The non-transitory computer-readable medium can be distributed over a plurality of computer systems connected to a network so that computer-readable code is written thereto and executed therefrom in a decentralized manner. Functional programs, code, and code segments for implementing the example embodiments can be readily deduced by programmers of ordinary skill in the art to which the present disclosure pertains.

The present disclosure has been described herein with regard to example embodiments. However, it will be obvious to those skilled in the art that various changes and modifications can be made without changing technical conception and features of the present disclosure. Thus, it is clear that the above-described example embodiments are illustrative in all aspects and are not intended to limit the present disclosure.

What is claimed is:

1. An apparatus for estimating bio-information, the apparatus comprising:
a sensor part including a pixel array of pixels, each pixel including a light source and a detector; and
a processor configured to:
based on an object being in contact with the sensor part, drive the sensor part based on a first sensor configuration;
obtain contact information of the object based on an amount of light received by each pixel according to the first sensor configuration;
determine a second sensor configuration based on the contact information;
drive the sensor part based on the second sensor configuration; and
estimate the bio-information based on light signals obtained according to the second sensor configuration.

2. The apparatus of claim 1, wherein the first sensor configuration comprises at least one of a time-division driving method, a sequential driving method, a simultaneous driving method, a driving order, a light source intensity, and a duration.

3. The apparatus of claim 1, wherein the processor is further configured to:
obtain the contact information based on at least one of a pixel having an amount of light being greater than or equal to a predetermined threshold value, a pixel having an amount of light being greater than or equal to a predetermined percentage of an average value of a total amount of light, a pixel having an amount of light being greater than or equal to a predetermined percentage of a maximum amount of light, and a pixel having an amount of light being greater than or equal to a predetermined percentage of an average value of an amount of light falling within a predetermined range of the maximum amount of light.

4. The apparatus of claim 1, wherein the processor is further configured to obtain the contact information including at least one of a contact area of the object, a center point of the contact area, a fingerprint center point, and a contact direction.

5. The apparatus of claim 4, wherein the processor is further configured to, based on the contact information, determine a light source pixel and a detector pixel of the second sensor configuration.

6. The apparatus of claim 5, wherein the processor is further configured to:
determine one or more pixels, located at predetermined positions in the contact direction, to be light source pixels of the second sensor configuration, among pixels in the contact area; and
determine one or more pixels, located within a predetermined range from the center point of the contact area or the fingerprint center point, to be detector pixels of the second sensor configuration.

7. The apparatus of claim 5, wherein the processor is further configured to:
map a reference area, a reference direction, and a reference center point of a pre-defined reference sensor configuration to the contact area, the contact direction, and the center point of the contact area; and
based on the mapping, determine pixels corresponding to light source pixels of the pre-defined reference sensor configuration to be the light source pixels of the second sensor configuration, and pixels corresponding to detector pixels of the pre-defined reference sensor configuration to be detector pixels of the second sensor configuration.

8. The apparatus of claim 4, wherein the sensor part is configured to obtain a fingerprint image based on the object being in contact with the sensor part, and wherein the processor is further configured to obtain the contact information based on the fingerprint image.

9. The apparatus of claim 8, wherein the processor is further configured to, based on the fingerprint center point not being located within a predetermined range of the sensor part, control an output interface to guide a user to place the object on the sensor part.

10. The apparatus of claim 1, wherein the processor is further configured to:
   determine a scattering coefficient based on the light signals obtained according to the second sensor configuration; and
   estimate the bio-information based on the scattering coefficient.

11. The apparatus of claim 1, wherein the processor is further configured to:
   based on the light signals being obtained according to the second sensor configuration, determine a similarity between the light signals; and
   select light signals, having the similarity being greater than or equal to a first threshold value, as light signals for estimating the bio-information.

12. The apparatus of claim 1, wherein the processor is further configured to:
   based on the light signals being obtained according to the second sensor configuration, determine a similarity between the light signals; and
   exclude light signals, having the similarity being less than or equal to a second threshold value, as light signals for estimating the bio-information.

13. The apparatus of claim 10, wherein the bio-information comprises at least one of triglyceride, body fat percentage, body water, blood glucose, cholesterol, carotenoid, protein, and uric acid.

14. A method of estimating bio-information, the method comprising:
   based on an object being in contact with a sensor part, driving the sensor part based on a first sensor configuration;
   obtaining contact information of the object based on an amount of light received by each pixel of the sensor part according to the first sensor configuration;
   determining a second sensor configuration based on the contact information;
   driving the sensor part based on the second sensor configuration; and
   estimating the bio-information based on light signals obtained according to the second sensor configuration.

15. The method of claim 14, wherein the obtaining the contact information comprises obtaining the contact information based on at least one of a pixel having an amount of light being greater than or equal to a predetermined threshold value, a pixel having an amount of light being greater than or equal to a predetermined percentage of an average value of a total amount of light, a pixel having an amount of light being greater than or equal to a predetermined percentage of a maximum amount of light, and a pixel having an amount of light being greater than or equal to a predetermined percentage of an average value of an amount of light falling within a predetermined range of the maximum amount of light.

16. The method of claim 14, wherein the obtaining the contact information comprises obtaining the contact information including at least one of a contact area of the object, a center point of the contact area, a fingerprint center point, and a contact direction.

17. The method of claim 16, wherein the determining the second sensor configuration comprises determining, based on the contact information, a light source pixel and a detector pixel of the second sensor configuration.

18. The method of claim 17, wherein the determining the second sensor configuration comprises:
   determining one or more pixels, located at predetermined positions in the contact direction, to be light source pixels of the second sensor configuration, among pixels in the contact area; and
   determining one or more pixels, located within a predetermined range from the center point of the contact area or the fingerprint center point, to be detector pixels of the second sensor configuration.

19. The method of claim 17, wherein the determining the second sensor configuration comprises:
   mapping a reference area, a reference direction, and a reference center point of a pre-defined reference sensor configuration to the contact area, the contact direction, and the center point of the contact area; and
   based on the mapping, determining pixels corresponding to light source pixels of the pre-defined reference sensor configuration to be the light source pixels of the second sensor configuration, and pixels corresponding to detector pixels of the pre-defined reference sensor configuration to be the detector pixels of the second sensor configuration.

20. The method of claim 17, further comprising:
   obtaining a fingerprint image based on the object being in contact with the sensor part,
   wherein the obtaining the contact information comprises obtaining the contact information based on the fingerprint image.

21. The method of claim 20, further comprising, based on the fingerprint center point not being located within a predetermined range of the sensor part, controlling an output interface to guide a user to place the object on the sensor part.

22. The method of claim 14, wherein the estimating the bio-information comprises:
   determining a scattering coefficient based on two or more light signals obtained by the sensor part; and
   estimating the bio-information based on the scattering coefficient.

23. The method of claim 14, wherein the estimating the bio-information comprises:
   based on the light signals being obtained by the sensor part, determining a similarity between the light signals; and
   selecting light signals, having the similarity being greater than or equal to a first threshold value, as light signals for estimating the bio-information.

24. The method of claim 14, wherein the estimating the bio-information comprises:
   based on the light signals being obtained by the sensor part, determining a similarity between the light signals; and
   excluding light signals, having the similarity being less than or equal to a second threshold value, as light signals for estimating the bio-information.

25. A method of estimating bio-information of a user, the method comprising:
   driving a first light source pixel and a first set of detector pixels of a pixel array of a sensor, based on a first sensor configuration;

identifying a contact area of the pixel array that is contact with an object of the user, based on driving the first light source pixel and the first set of detector pixels;
identifying a second sensor configuration based on the contact area;
driving a second light source pixel and a second set of detector pixels of the pixel array of the sensor, based on the second sensor configuration; and
obtaining light signals based on driving the second light source pixel and the second set of detector pixels; and
estimating the bio-information of the user based on the light signals.

* * * * *